United States Patent
Wang et al.

(10) Patent No.: US 12,168,752 B2
(45) Date of Patent: Dec. 17, 2024

(54) HIGH-TEMPERATURE VISUAL ACID ETCHING EXPERIMENTAL DEVICE AND METHOD

(71) Applicant: Southwest Petroleum University, Sichuan (CN)

(72) Inventors: Kun Wang, Chengdu (CN); Shouxin Wang, Chengdu (CN); Jianchun Guo, Chengdu (CN); Chi Chen, Chengdu (CN); Tao Zhang, Chengdu (CN); Xiang Bai, Chengdu (CN); Xinghao Gou, Chengdu (CN); Jichuan Ren, Chengdu (CN); Cong Lu, Sichuan (CN); Bo Gou, Chengdu (CN); Jie Lai, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 18/402,787

(22) Filed: Jan. 3, 2024

(65) Prior Publication Data
US 2024/0228864 A1   Jul. 11, 2024

(51) Int. Cl.
*C09K 8/72* (2006.01)

(52) U.S. Cl.
CPC ...................... *C09K 8/72* (2013.01)

(58) Field of Classification Search
CPC ....................................... C09K 8/72
See application file for complete search history.

(56) References Cited

FOREIGN PATENT DOCUMENTS

| CN | 202196059 U | * | 4/2012 | |
|---|---|---|---|---|
| CN | 106437671 | | 2/2017 | |
| CN | 106437671 A | * | 2/2017 | ............. E21B 43/26 |

* cited by examiner

*Primary Examiner* — Kumar R Bhushan
(74) *Attorney, Agent, or Firm* — JMB Davis Ben-David

(57) ABSTRACT

The present invention discloses a novel high-temperature visual acid etching test device and method; the test device includes a visual rock slab holder, an acid solution storage tank I, an acid solution storage tank II, a heating apparatus, a high-pressure water pump, a low-pressure acid pump, a back-pressure valve, an acid valve A, an acid valve B, an acid valve C, an acid valve D, an acid valve E, an acid valve F, a water valve G, a water valve H, a water valve I, a water valve J, and a water valve K; both the acid solution storage tank I and the acid solution storage tank II are provided with a piston therein, where the acid solution storage tank is divided into upper and lower independent parts by the piston. According to the present invention, the flowing process of an acid solution in a fracture can be directly observed to accurately characterize the distribution of the acid solution in the fracture, which facilitates a study on an acid etching mechanism. According to the present invention, an acid solution injection system is separated from a water injection system, so that only water is injected into the system through a high-pressure pump, effectively solving safety problems of acid solution pumping. In the test process of the present invention, a totally-enclosed acid solution system can ensure that the acid solution does not overflow at high temperature and high pressure, thus greatly increasing the safety of the test.

9 Claims, 1 Drawing Sheet

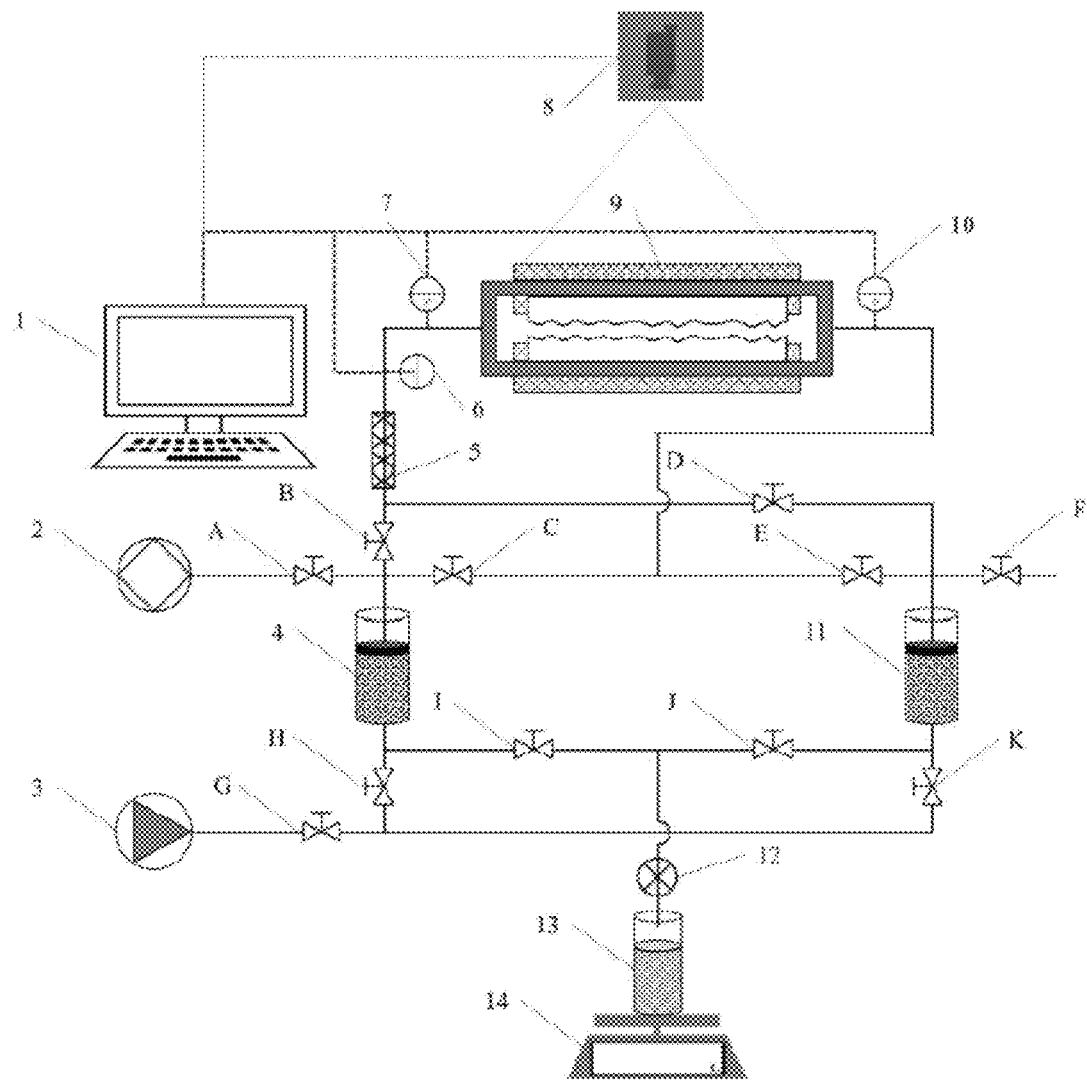

HIGH-TEMPERATURE VISUAL ACID ETCHING EXPERIMENTAL DEVICE AND METHOD

TECHNICAL FIELD

The present invention relates to a novel high-temperature visual acid etching test device and method, and pertains to the technical field of petroleum and gas stimulation and geotechnical engineering.

BACKGROUND

Acid fracturing is an indispensable way for stimulation of carbonate reservoirs. Acid fracturing technology features that a formation fracture surface is unevenly etched through an acid solution to form an oil-gas flowing space incompletely enclosed under pressure, thereby achieving the stimulation purpose. The flow conductivity of acid-etched fractures is a key indicator to evaluate acid fracturing and mainly depends on the acid etching morphology of the acid-etched fractures.

At present, the acid etching effect and the flow conductivity of acid-etched fractures are evaluated mainly through an indoor test method. In conventional indoor tests, underground cores or outcropped rocks at a same formation are used to fabricate rock slabs with smooth and straight surfaces to simulate formation fractures and test the acid etching and the flow conductivity of acid-etched fractures, thereby analyzing the influence of different geological parameters and construction parameters on the fracture surface acid etching morphology and the flow conductivity of acid-etched fractures. However, the roughness of the actual formation fracture surface is relatively large, and many different-size micro-protrusions are distributed on the fracture surface. Therefore, the acid etching morphology of the carbonate reservoir and the flow conductivity of acid-etched fractures cannot be accurately evaluated through a conventional indoor slab test, and the actual formation conditions cannot be reflected through the test results. This leads to great deviation in prediction of fracture conductivity and inaccurate acid fracturing prediction effect and affects the implementation of the acid fracturing technology.

In addition, China gradually develops the carbonate reservoirs towards deep and ultra-deep carbonate reservoirs; the reservoir temperature and the formation pressure are gradually rising, and the reservoir temperature is generally above 120° C. The highest temperature of the deep carbonate reservoirs in Sichuan Basin is up to 212° C. As the deep carbonate reservoirs in China are distinctive, the existing acid etching test devices used in laboratories have the following limitations: firstly, the exiting acid etching test devices are mainly used at normal temperature and pressure, so the simulated temperature cannot meet the requirements of deep and ultra-deep carbonate reservoirs; secondly, the existing test devices cannot be used to directly observe the flowing and etching process of an acid solution in the fracture, so that the numerical simulation results cannot be verified; thirdly, the high-temperature acid solution in the existing test devices has the risk of overflow during the test, so there are great safety risks; fourthly, the existing test devices cannot realize the circulating pumping of the limited acid solution, so the test materials are greatly lost and wasted. In order to accurately simulate the real underground situation and directly observe the flowing and etching process of the acid solution in the fracture, a novel high-temperature visual acid etching test device is innovated in this study.

SUMMARY

To overcome the problems in the prior art, the present invention provides a novel high-temperature visual acid etching test device and method. According to the method, the high-temperature visual acid etching test device is used in the method, pseudo-three-dimensional rough rock samples are fabricated to carry out the acid etching test; the flowing behavior of an acid solution in the fracture is observed and analyzed under different test conditions, so as to define the influence rule of initial roughness of a fracture surface on the acid etching morphology of acid etching fractures and reveal the acid etching mechanism of non-planar fractures.

To solve the technical problems, a technical solution provided by the present invention is that a novel high-temperature visual acid etching test device is provided, and the device includes a visual rock slab holder, an acid solution storage tank I, an acid solution storage tank II, a heating apparatus, a high-pressure water pump, a low-pressure acid pump, a back-pressure valve, an acid valve A, an acid valve B, an acid valve C, an acid valve D, an acid valve E, an acid valve F, a water valve G, a water valve H, a water valve I, a water valve J, and a water valve K.

Both the acid solution storage tank I and the acid solution storage tank II are provided with a piston therein, where the acid solution storage tank is divided into upper and lower independent parts by the piston.

The upper end of the heating apparatus is connected with the left end of the visual rock slab holder; the lower end thereof is respectively connected with the upper end of the acid valve B and the left end of the acid valve D; the right end of the visual rock slab holder is respectively connected with the right end of the acid valve C and the left end of the acid valve E; a thermometer and a pressure meter I are arranged between the heating apparatus and the visual rock slab holder; a pressure meter II is arranged on the right end of the visual rock slab holder.

The low-pressure acid pump is connected with the left end of the acid valve A; the upper end of the acid solution storage tank I is respectively connected with the right end of the acid valve A, the lower end of the acid valve B, and the left end of the acid valve C; the upper end of the acid solution storage tank II is respectively connected with the right end of the acid valve E, the left end of the acid valve F, and the right end of the acid valve D; an emptying pipeline is arranged on the right end of the acid valve F.

The high-pressure water pump is connected with the left end of the water valve G; the right end of the water valve G is respectively connected with the lower end of the water valve H and the lower end of the water valve K; the lower end of the acid solution storage tank I is connected with the upper end of the water valve H and the left end of the water valve I; the lower end of the acid solution storage tank II is respectively connected with the right end of the water valve J and the upper end of the water valve K; the upper end of the back-pressure valve is respectively connected with the right end of the water valve I and the left end of the water valve J; and an acid solution discharge pipeline is arranged on the lower end thereof.

A further technical solution is that the test device further includes a height camera, where the height camera is located above the visual rock slab holder to identify and acquire images during flowing and etching of an acid solution in the fracture of the visual rock slab holder.

A further technical solution is that the test device further includes a computer, where the computer is electrically connected with the thermometer, the pressure meter I, the height camera, and the pressure meter II, respectively.

A further technical solution is that the high-pressure water pump is a constant-flux pump with the flow rate of 0-1 L/min and the pressure of 10 MPa.

A further technical solution is that the low-pressure acid pump is a peristaltic pump with the flow rate of 0-0.4 L/min and the pressure of 0.1 MPa.

A further technical solution is that the calculation formula of the circulating acid solution reserve of the acid solution storage tank is as follows:

$$V = \frac{JS\Delta t}{2(c_1 - c_2)} \quad (1)$$

In the formula, V denotes the circulating acid solution reserve of the acid solution storage tank, in an unit of L; J denotes a reaction rate, in an unit of mol/(cm²·h); $\Delta t$ denotes an acid injection time, in an unit of h; S denotes a contact surface area between a sample and an acid solution, in an unit of cm²; $c_1$ denotes the concentration of the acid solution before acid injection, in an unit of mol/L; $c_2$ denotes the concentration of the acid solution after acid injection, in an unit of mol/L; (when $$\frac{c_1 - c_2}{c_1} \leq 3\%$$

is satisfied, it is considered that the reaction speed of acid rock is constant).

A further technical solution is that the heating apparatus is a heating runner.

A further technical solution is that the test device further includes a recycling tank connected with the acid solution discharge pipeline.

A further technical solution is that the test device further includes a balance, where the recycling tank is located on the balance.

A further technical solution is that pipelines connected between components are made of Hastelloy alloy.

A further technical solution is that the observation window of the visual rock slab holder is made of high-temperature resistant glass material.

A further technical solution is that the output end of the pipeline connected with a liquid inlet and the input end of the pipeline connected with a liquid outlet are both flared.

A novel high-temperature visual acid etching test method is provided, and the method includes the following steps:

Step S1: selecting a core of a target block; and cutting the core until the size thereof matches with a visual rock slab holder.

Step S2: loading the core into the visual rock slab holder setting the initial fracture width of the core.

Step S3: setting an acid solution displacement consistent with a field displacement; and obtaining an acid injection volume according to the acid solution displacement and an acid injection time.

Step S4: turning on an acid valve A and a water valve I; setting the pressure of a back-pressure valve to 0 MPa; activating a low-pressure acid pump to inject an acid solution into an acid solution storage tank I; and detecting the acid solution flow at the outlet of the back-pressure valve until the acid solution storage tank I is filled with the acid solution.

Step S5: turning on a water valve G, a water valve K, and an acid valve F; activating a high-pressure water pump to inject water into an acid solution storage tank II until the acid solution storage tank II is filled with the water.

Step S6: turning on an acid valve B, an acid valve E, the water valve G, a water valve H, and a water valve J; setting the pressure of the back-pressure valve to 8 MPa; activating a heating apparatus to heat a temperature to 200° C.; activating the high-pressure water pump to inject the water into the acid solution storage tank I, that is, injecting the water into the acid solution storage tank I to inject the acid solution in the acid solution storage tank I into the left end of the visual rock slab holder, and injecting the acid solution in the right end of the visual rock slab holder into the acid solution storage tank II under pressure; and discharging the water in the acid solution storage tank II through the back-pressure valve until the acid solution storage tank I is filled with the water.

Step S7: turning on an acid valve C, an acid valve D, the water valve G, the water valve I, and the water valve K; setting the pressure of the back-pressure valve to 8 MPa; activating the heating apparatus to heat the temperature to 200° C.; activating the high-pressure water pump to inject the water into the acid solution storage tank II, that is, injecting the water into the acid solution storage tank II to inject the acid solution in the acid solution storage tank II into the left end of the visual rock slab holder, and injecting the acid solution in the right end of the visual rock slab holder into the acid solution storage tank I; and discharging the water in the acid solution storage tank I through the back-pressure valve until the acid solution storage tank II is filled with the water.

Step S8: repeating Step S6 and Step S7 to implement cyclic acid injection.

Step S9: ending up the test; performing pressure relief; activating the acid valve C, the acid valve E, and the acid valve F; turning on the water valve G, the water valve H, and the water valve K; and activating the high-pressure water pump to wash the tank and discharge the acid solution.

Step S10: turning on the acid valve A, the acid valve B, the acid valve C, the acid valve D, the acid valve E, and the acid valve F; activating the high-pressure water pump; fetching water to clean a pipeline; after pipeline cleaning, purging the pipeline of an acid solution system with compressed air; and restoring the system to an initial state.

The present invention has the following beneficial effects:

1. According to the present invention, the flowing process of an acid solution in a fracture can be directly observed to accurately characterize the distribution of the acid solution in the fracture, which facilitates a study on an acid etching mechanism.

2. According to the present invention, an acid solution injection system is separated from a water injection system, so that only water is injected to the system through a high-pressure pump, effectively solving safety problems of acid solution pumping.

3. In the test process of the present invention, a totally-enclosed acid solution system can ensure that the acid solution does not overflow at high temperature and high pressure, thus greatly increasing the safety of the test.

4. According to the present invention, the acid solution storage tank 1 and the acid solution storage tank 2 are connected to implement the circulating reversal of the acid solution, ensuring the unchanged flow direction of the acid solution in the visual rock slab holder, which realizes the circulating pumping of the limited acid solution and correspondingly prolongs the test time.

5. All systems of the present invention are fully fixed, and only the visual rock slab holder can be disassembled to reduce personnel operation and ensure long-term stability of equipment.

BRIEF DESCRIPTION OF DRAWINGS

FIG. 1 is a schematic structural diagram according to the present invention.

As shown in the figure: 1—computer; 2—low-pressure acid pump; 3—high-pressure water pump; 4—acid solution storage tank I; 5—heating apparatus; 6—thermometer; 7—pressure meter I; 8—height camera; 9—visual rock slab holder; 10—pressure meter II; 11—acid solution storage tank II; 12—back-pressure valve; 13—waste liquid recycling tank; and 14—balance.

DESCRIPTION OF EMBODIMENTS

The following will clearly and completely describe the technical solutions of the present invention with reference to accompanying drawings. Apparently, the described embodiments are some embodiments of the present invention rather than all embodiments thereof. Based on the embodiments of the present invention, all other embodiments obtained by persons of ordinary skill in the art without creative labor fall within the protection scope of the present invention.

As shown in FIG. 1, a novel high-temperature visual acid etching test device provided in the present invention includes a visual rock slab holder 9, an acid solution storage tank I 4, an acid solution storage tank II 11, a heating apparatus 5, a high-pressure water pump 3, a low-pressure acid pump 2, a back-pressure valve 12, an acid valve A, an acid valve B, an acid valve C, an acid valve D, an acid valve E, an acid valve F, a water valve G, a water valve H, a water valve I, a water valve J, and a water valve K; both the acid solution storage tank I 4 and the acid solution storage tank II 11 are provided with a piston therein, where the acid solution storage tank is divided into upper and lower independent parts by the piston; an acid solution and water are capable to be respectively injected into the upper and lower parts; the upper end of the heating apparatus is connected with the left end of the visual rock slab holder 9; the lower end thereof is respectively connected with the upper end of the acid valve B and the left end of the acid valve D; the right end of the visual rock slab holder 9 is respectively connected with the right end of the acid valve C and the left end of the acid valve E; a thermometer 6 and a pressure meter I 7 are arranged between the heating apparatus 5 and the visual rock slab holder 9; a pressure meter II 10 is arranged on the right end of the visual rock slab holder 9; the low-pressure acid pump 2 is connected with the left end of the acid valve A; the upper end of the acid solution storage tank I 4 is respectively connected with the right end of the acid valve A, the lower end of the acid valve B, and the left end of the acid valve C; the upper end of the acid solution storage tank II 11 is respectively connected with the right end of the acid valve E, the left end of the acid valve F, and the right end of the acid valve D; an emptying pipeline is arranged on the right end of the acid valve F; the high-pressure water pump 3 is connected with the left end of the water valve G; the right end of the water valve G is respectively connected with the lower end of the water valve H and the lower end of the water valve K; the lower end of the acid solution storage tank I 4 is connected with the upper end of the water valve H and the left end of the water valve I; the lower end of the acid solution storage tank II 11 is respectively connected with the right end of the water valve J and the upper end of the water valve K; the upper end of the back-pressure valve 12 is respectively connected with the right end of the water valve I and the left end of the water valve J; and an acid solution discharge pipeline is arranged on the lower end thereof. In this embodiment, the high-pressure water pump 3 is a constant-flux pump with the flow rate of 0-1 L/min and the pressure of 10 MPa; and the low-pressure acid pump 2 is a peristaltic pump with the flow rate of 0-0.4 L/min and the pressure of 0.1 MPa.

In this embodiment, the calculation results of the circulating acid solution reserve of the acid solution storage tank are as shown in Table 1.

TABLE 1

Calculation results of circulating acid solution reserve of acid solution storage tank

| Reaction rate mol/(cm² · s) | Reaction time (min) | Specimen surface area (cm²) | Initial concentration (mol/L) | Circulating acid solution reserve (L) |
|---|---|---|---|---|
| 1 × 10⁻⁶ | 10 | 64.08 | 1 | 0.64 |
| | 20 | 64.08 | | 1.28 |
| | 30 | 64.08 | | 1.92 |
| | 60 | 64.08 | | 3.84 |
| | 90 | 64.08 | | 5.77 |
| | 120 | 64.08 | | 7.69 |
| | 10 | 64.08 | 3 | 0.21 |
| | 20 | 64.08 | | 0.43 |
| | 30 | 64.08 | | 0.64 |
| | 60 | 64.08 | | 1.28 |
| | 90 | 64.08 | | 1.92 |
| | 120 | 64.08 | | 2.56 |
| | 10 | 64.08 | 5 | 0.13 |
| | 20 | 64.08 | | 0.26 |
| | 30 | 64.08 | | 0.38 |
| | 60 | 64.08 | | 0.77 |
| | 90 | 64.08 | | 1.15 |
| | 120 | 64.08 | | 1.54 |
| 3 × 10⁻⁶ | 10 | 64.08 | 1 | 1.92 |
| | 20 | 64.08 | | 3.84 |
| | 30 | 64.08 | | 5.77 |
| | 60 | 64.08 | | 11.53 |
| | 90 | 64.08 | | 17.30 |
| | 120 | 64.08 | | 23.07 |
| | 10 | 64.08 | 3 | 0.64 |
| | 20 | 64.08 | | 1.28 |
| | 30 | 64.08 | | 1.92 |
| | 60 | 64.08 | | 3.84 |
| | 90 | 64.08 | | 5.77 |
| | 120 | 64.08 | | 7.69 |
| | 10 | 64.08 | 5 | 0.38 |
| | 20 | 64.08 | | 0.77 |
| | 30 | 64.08 | | 1.15 |
| | 60 | 64.08 | | 2.31 |
| | 90 | 64.08 | | 3.46 |
| | 120 | 64.08 | | 4.61 |
| 5 × 10⁻⁶ | 10 | 64.08 | 1 | 3.20 |
| | 20 | 64.08 | | 6.41 |
| | 30 | 64.08 | | 9.61 |
| | 60 | 64.08 | | 19.22 |
| | 90 | 64.08 | | 28.84 |
| | 120 | 64.08 | | 38.45 |
| | 10 | 64.08 | 3 | 1.07 |
| | 20 | 64.08 | | 2.14 |
| | 30 | 64.08 | | 3.20 |
| | 60 | 64.08 | | 6.41 |
| | 90 | 64.08 | | 9.61 |
| | 120 | 64.08 | | 12.82 |
| | 10 | 64.08 | 5 | 0.64 |
| | 20 | 64.08 | | 1.28 |

TABLE 1-continued

Calculation results of circulating acid solution reserve of acid solution storage tank

| Reaction rate mol/(cm² · s) | Reaction time (min) | Specimen surface area (cm²) | Initial concentration (mol/L) | Circulating acid solution reserve (L) |
|---|---|---|---|---|
| | 30 | 64.08 | | 1.92 |
| | 60 | 64.08 | | 3.84 |
| | 90 | 64.08 | | 5.77 |
| | 120 | 64.08 | | 7.69 |

As shown in FIG. 1, based on this embodiment, the test device further includes a height camera 8, where the height camera 8 is located above the visual rock slab holder 9 and constitutes into an image acquisition and analysis system with a computer 1 to identify and acquire images during flowing and etching of an acid solution in the fracture of the visual rock slab holder; the test device further includes the computer 1, where the computer 1 is electrically connected with the thermometer 6, the pressure meter I 7, the height camera 8, and the pressure meter II 10, respectively; and the computer 1 is used to monitor the acid etching state in real time.

In this embodiment, the heating apparatus 5 is a heating runner.

As shown in FIG. 1, based on this embodiment, the test device further includes a recycling tank 13 connected with the acid solution discharge pipeline, and a balance 14, where the recycling tank 13 is located on the balance 14, so that the weight of water discharged from the tank is weighed by the balance 14 each time.

The specific implementation process of this embodiment is as follows:

Step S1: selecting a core of a target block; and cutting the core until the size thereof matches with a visual rock slab holder 9.

Step S2: loading the core into the visual rock slab holder setting the initial fracture width of the core.

Step S3: setting an acid solution displacement consistent with a field displacement; and obtaining an acid injection volume according to the acid solution displacement and an acid injection time.

Step S4: turning on an acid valve A and a water valve I; setting the pressure of a back-pressure valve 12 to 0 MPa; activating a low-pressure acid pump 2 to inject an acid solution into an acid solution storage tank I 4; and detecting the acid solution flow at the outlet of the back-pressure valve until the acid solution storage tank I is filled with the acid solution.

Step S5: turning on a water valve G, a water valve K, and an acid valve F; activating a high-pressure water pump to inject water into an acid solution storage tank II 11 until the acid solution storage tank II is filled with the water.

Step S6: turning on an acid valve B, an acid valve E, the water valve G, a water valve H, and a water valve J; setting the pressure of the back-pressure valve 12 to 8 MPa; activating a heating apparatus 5 to heat a temperature to 200° C.; activating the high-pressure water pump 3 to inject the water into the acid solution storage tank I 4, that is, injecting the water into the acid solution storage tank I 4 to inject the acid solution in the acid solution storage tank I 4 into the left end of the visual rock slab holder 9, and injecting the acid solution in the right end of the visual rock slab holder 9 into the acid solution storage tank II 11 under pressure; and discharging the water in the acid solution storage tank II 11 through the back-pressure valve 12 until the acid solution storage tank I 4 is filled with the water.

Step S7: turning on an acid valve C, an acid valve D, the water valve G, the water valve I, and the water valve K; setting the pressure of the back-pressure valve 12 to 8 MPa; activating the heating apparatus 5 to heat the temperature to 200° C.; activating the high-pressure water pump 3 to inject the water into the acid solution storage tank II 11, that is, injecting the water into the acid solution storage tank II 11 to inject the acid solution in the acid solution storage tank II 11 into the left end of the visual rock slab holder 9, and injecting the acid solution in the right end of the visual rock slab holder 9 into the acid solution storage tank I 4; and discharging the water in the acid solution storage tank I 4 through the back-pressure valve 12 until the acid solution storage tank II 11 is filled with the water.

Step S8: repeating Step S6 and Step S7 to implement cyclic acid injection.

Step S9: ending up the test; performing pressure relief; activating the acid valve C, the acid valve E, and the acid valve F; turning on the water valve G, the water valve H, and the water valve K; and activating the high-pressure water pump 3 to wash the tank and discharge the acid solution.

Step S10: turning on the acid valve A, the acid valve B, the acid valve C, the acid valve D, the acid valve E, and the acid valve F; activating the high-pressure water pump 3; fetching water to clean a pipeline; after pipeline cleaning, purging the pipeline of an acid solution system with compressed air; and restoring the system to an initial state.

The foregoing descriptions are not intended to limit the present invention in any form. Although the present invention has been disclosed by the above embodiments, they are not intended to limit the present invention. Any person skilled in the art can, without departing from the scope of the technical solution of the present invention, make some changes or modify them into equivalent embodiments of equivalent changes according to the technical contents disclosed above. However, any simple alterations, equivalent changes and modifications made to the above embodiments according to the technical essence of the present invention without departing from the technical solution of the present invention will still fall within the scope of the technical solution of the present invention.

The invention claimed is:

1. A novel high-temperature visual acid etching test device, comprising a visual rock slab holder (9), an acid solution storage tank I (4), an acid solution storage tank II (11), a heating apparatus (5), a high-pressure water pump (3), a low-pressure acid pump (2), a back-pressure valve (12), an acid valve A, an acid valve B, an acid valve C, an acid valve D, an acid valve E, an acid valve F, a water valve G, a water valve H, a water valve I, a water valve J, and a water valve K;

both the acid solution storage tank I (4) and the acid solution storage tank II (11) are provided with a piston therein, wherein the acid solution storage tank is divided into upper and lower independent parts by the piston; an acid solution and water are capable to be respectively injected into the upper and lower parts;

the upper end of the heating apparatus (5) is connected with the left end of the visual rock slab holder (9); the lower end thereof is respectively connected with the upper end of the acid valve B and the left end of the acid valve D; the right end of the visual rock slab holder (9) is respectively connected with the right end of the acid valve C and the left end of the acid valve E; a thermometer (6) and a pressure meter I (7) are arranged between the heating apparatus (5) and the visual rock slab holder (9); a pressure meter II (10) is arranged on the right end of the visual rock slab holder (9);

the low-pressure acid pump (2) is connected with the left end of the acid valve A;

the upper end of the acid solution storage tank I (4) is respectively connected with the right end of the acid valve A, the lower end of the acid valve B, and the left end of the acid valve C; the upper end of the acid solution storage tank II (11) is respectively connected with the right end of the acid valve E, the left end of the acid valve F, and the right end of the acid valve D; an emptying pipeline is arranged on the right end of the acid valve F;

the high-pressure water pump (3) is connected with the left end of the water valve G; the right end of the water valve G is respectively connected with the lower end of the water valve H and the lower end of the water valve K; the lower end of the acid solution storage tank I (4) is connected with the upper end of the water valve H and the left end of the water valve I; the lower end of the acid solution storage tank II (11) is respectively connected with the right end of the water valve J and the upper end of the water valve K; the upper end of the back-pressure valve (12) is respectively connected with the right end of the water valve I and the left end of the water valve J; and an acid solution discharge pipeline is arranged on the lower end thereof.

2. The novel high-temperature visual acid etching test device according to claim 1, further comprising a height camera (8), wherein the height camera (8) is located above the visual rock slab holder (9) to identify and acquire images during flowing and etching of the acid solution in the fracture of the visual rock slab holder (9).

3. The novel high-temperature visual acid etching test device according to claim 2, further comprising a computer (1), wherein the computer (1) is electrically connected with the thermometer (6), the pressure meter I (7), the height camera (8), and the pressure meter II (10), respectively.

4. The novel high-temperature visual acid etching test device according to claim 1, wherein the high-pressure water pump (3) is a constant-flux pump with the flow rate of 0-1 L/min and the pressure of 10 MPa.

5. The novel high-temperature visual acid etching test device according to claim 1, wherein the low-pressure acid pump (2) is a peristaltic pump with the flow rate of 0-0.4 L/min and the pressure of 0.1 MPa.

6. The novel high-temperature visual acid etching test device according to claim 1, wherein the heating apparatus (5) is a heating runner.

7. The novel high-temperature visual acid etching test device according to claim 1, further comprising a recycling tank (13) connected with the acid solution discharge pipeline.

8. The novel high-temperature visual acid etching test device according to claim 7, further comprising a balance (14), wherein the recycling tank (13) is located on the balance (14).

9. A novel high-temperature visual acid etching test method, wherein the novel high-temperature visual acid etching test device according to any one of claims 1 to 8 is used in the method, and the method specifically comprises the following steps:

Step S1: selecting a core of a target block; and cutting the core until the size thereof matches with a visual rock slab holder (9);

Step S2: loading the core into the visual rock slab holder (9) and setting the initial fracture width of the core;

Step S3: setting an acid solution displacement consistent with a field displacement; and obtaining an acid injection volume according to the acid solution displacement and an acid injection time;

Step S4: turning on an acid valve A and a water valve I; setting the pressure of a back-pressure valve (12) to 0 MPa; activating a low-pressure acid pump (2) to inject an acid solution into an acid solution storage tank I (4); and detecting the acid solution flow at the outlet of the back-pressure valve until the acid solution storage tank I is filled with the acid solution;

Step S5: turning on a water valve G, a water valve K, and an acid valve F; activating a high-pressure water pump (3) to inject water into an acid solution storage tank II (11) until the acid solution storage tank II is filled with the water;

Step S6: turning on an acid valve B, an acid valve E, the water valve G, a water valve H, and a water valve J; setting the pressure of the back-pressure valve (12) to 8 MPa; activating a heating apparatus (5) to heat a temperature to 200° C.; activating the high-pressure water pump (3) to inject the water into the acid solution storage tank I (4), that is, injecting the water into the acid solution storage tank I (4) to inject the acid solution in the acid solution storage tank I (4) into the left end of the visual rock slab holder (9), and injecting the acid solution in the right end of the visual rock slab holder (9) into the acid solution storage tank II (11) under pressure; and discharging the water in the acid solution storage tank II (11) through the back-pressure valve (12) until the acid solution storage tank I (4) is filled with the water;

Step S7: turning on an acid valve C, an acid valve D, the water valve G, the water valve I, and the water valve K; setting the pressure of the back-pressure valve (12) to 8 MPa; activating the heating apparatus (5) to heat the temperature to 200° C.; activating the high-pressure water pump (3) to inject the water into the acid solution storage tank II (11), that is, injecting the water into the acid solution storage tank II (11) to inject the acid solution in the acid solution storage tank II (11) into the left end of the visual rock slab holder (9), and injecting the acid solution in the right end of the visual rock slab holder (9) into the acid solution storage tank I (4); and discharging the water in the acid solution storage tank I (4) through the back-pressure valve (12) until the acid solution storage tank II (11) is filled with the water;

Step S8: repeating Step S6 and Step S7 to implement cyclic acid injection;

Step S9: ending up the test; performing pressure relief; activating the acid valve C, the acid valve E, and the acid valve F; turning on the water valve G, the water valve H, and the water valve K; and activating the high-pressure water pump (3) to wash the tank and discharge the acid solution; and Step S10: turning on the acid valve A, the acid valve B, the acid valve C, the acid valve D, the acid valve E, and the acid valve F; activating the high-pressure water pump (3); fetching water to clean a pipeline; after pipeline cleaning, purging the pipeline of an acid solution system with compressed air; and restoring the system to an initial state.

* * * * *